United States Patent [19]

Green

[11] Patent Number: 4,580,712

[45] Date of Patent: Apr. 8, 1986

[54] SURGICAL FASTENER APPLYING APPARATUS WITH PROGRESSIVE APPLICATION OF FASTENER

[75] Inventor: David T. Green, Norwalk, Conn.

[73] Assignee: United States Surgical Corporation, Norwalk, Conn.

[21] Appl. No.: 662,679

[22] Filed: Oct. 19, 1984

[51] Int. Cl.[4] ............................................. A61B 17/00
[52] U.S. Cl. ................................ 227/19; 128/334 R; 227/DIG. 1
[58] Field of Search ............. 128/334 R; 227/DIG. 1, 227/19, 135, 136

[56] References Cited

U.S. PATENT DOCUMENTS

| 960,300 | 6/1910 | Fischer | 227/DIG. 1 |
|---|---|---|---|
| 2,344,071 | 3/1944 | Wilson et al. | 227/DIG. 1 |
| 3,078,465 | 2/1963 | Bobrov | 227/DIG. 1 |
| 3,079,606 | 3/1963 | Bobrov et al. | 227/DIG. 1 |
| 3,317,105 | 5/1967 | Astafjev et al. | 227/76 |
| 3,490,675 | 1/1970 | Green et al. | 227/19 |
| 3,499,591 | 3/1970 | Green | 227/76 |
| 4,111,206 | 9/1978 | Vishnevsky et al. | 128/305 |
| 4,241,861 | 12/1980 | Fleischer | 227/135 |
| 4,244,372 | 1/1981 | Kapitanov et al. | 128/334 R |
| 4,290,542 | 9/1981 | Fedotov et al. | 227/155 |
| 4,429,695 | 2/1984 | Green | 128/305 |
| 4,475,679 | 10/1984 | Fleury | 227/19 |

FOREIGN PATENT DOCUMENTS 927936 6/1963 United Kingdom .
1158113 7/1969 United Kingdom .

Primary Examiner—Paul A. Bell
Attorney, Agent, or Firm—Robert R. Jackson; John E. Nathan

[57] ABSTRACT

An apparatus for applying a relatively large number of surgical fasteners to body tissue, application of some fasteners is made to precede application of other fasteners in order to spread out and thereby reduce the peak fastener applying load or force.

7 Claims, 13 Drawing Figures

SURGICAL FASTENER APPLYING APPARATUS WITH PROGRESSIVE APPLICATION OF FASTENER

BACKGROUND OF THE INVENTION

This invention relates to apparatus for applying surgical fasteners to body tissue, and more particularly to apparatus for applying a relatively large number of such fasteners substantially simultaneously.

Instruments for applying relatively large numbers of surgical fasteners simultaneously or substantially simultaneously are known as shown, for example, by Hirsch et al. U.S. Pat. No. 3,275,211, Green U.S. Pat. No. 4,402,444, and Green U.S. Pat. No. 4,402,445. The fasteners may take the form of metal surgical staples as shown in the Hirsch et al. patent, or they may be initially two-part non-metallic surgical fasteners as shown in the Green U.S. Pat. No. 4,402,445. The term "surgical fasteners" is used herein as a generic term for both of these types of fasteners.

Some surgical procedures require the application of a very large number of surgical fasteners. For example, the device shown in the Green U.S. Pat. No. 4,402,444 is adapted to apply 50, 60, or even more fasteners in four closely spaced rows. If all of these fasteners are driven exactly simultaneously, the peak force required can be very large. This necessitates an instrument design which is very strong and correspondingly costly. It also may make this instrument relatively difficult to operate.

It is therefore an object of this invention to reduce the peak force required in instruments which apply relatively large numbers of surgical fasteners.

SUMMARY OF THE INVENTION

This and other objects of the invention are accomplished in accordance with the principles of the invention by providing surgical fastener applying apparatus including means for causing one end of a rigid member in the fastener driving assembly to initially move faster in the fastener driving direction than the other end of that member initially moves so that application of the fasteners adjacent said one end of the member precedes application of the fasteners adjacent said other end of the member. In this way the fastener applying load is distributed over time so that the peak force required is reduced as compared to the peak force required for applying all of the fasteners exactly simultaneously.

Further features of the invention, its nature and various advantages will be more apparent from the accompanying drawings and the following detailed description of the invention.

BRIEF DESCRIPTION OF THE DRAWINGS

FIG. 4 is a partial exploded perspective view of the apparatus of FIGS. 1-3.

DETAILED DESCRIPTION OF THE INVENTION

Among the environments in which the present invention can be employed are the articulated surgical fastener applying instruments shown in concurrently filed U.S. patent application Ser. No. 662,677. One of those instruments (shown in FIGS. 1-12 herein, which are respectively identical to FIGS. 1-12 in the above-mentioned concurrently filed application) will first be described in detail. Then, modification of that device in accordance with the present invention will be described with reference to FIG. 13.

Figure 1:
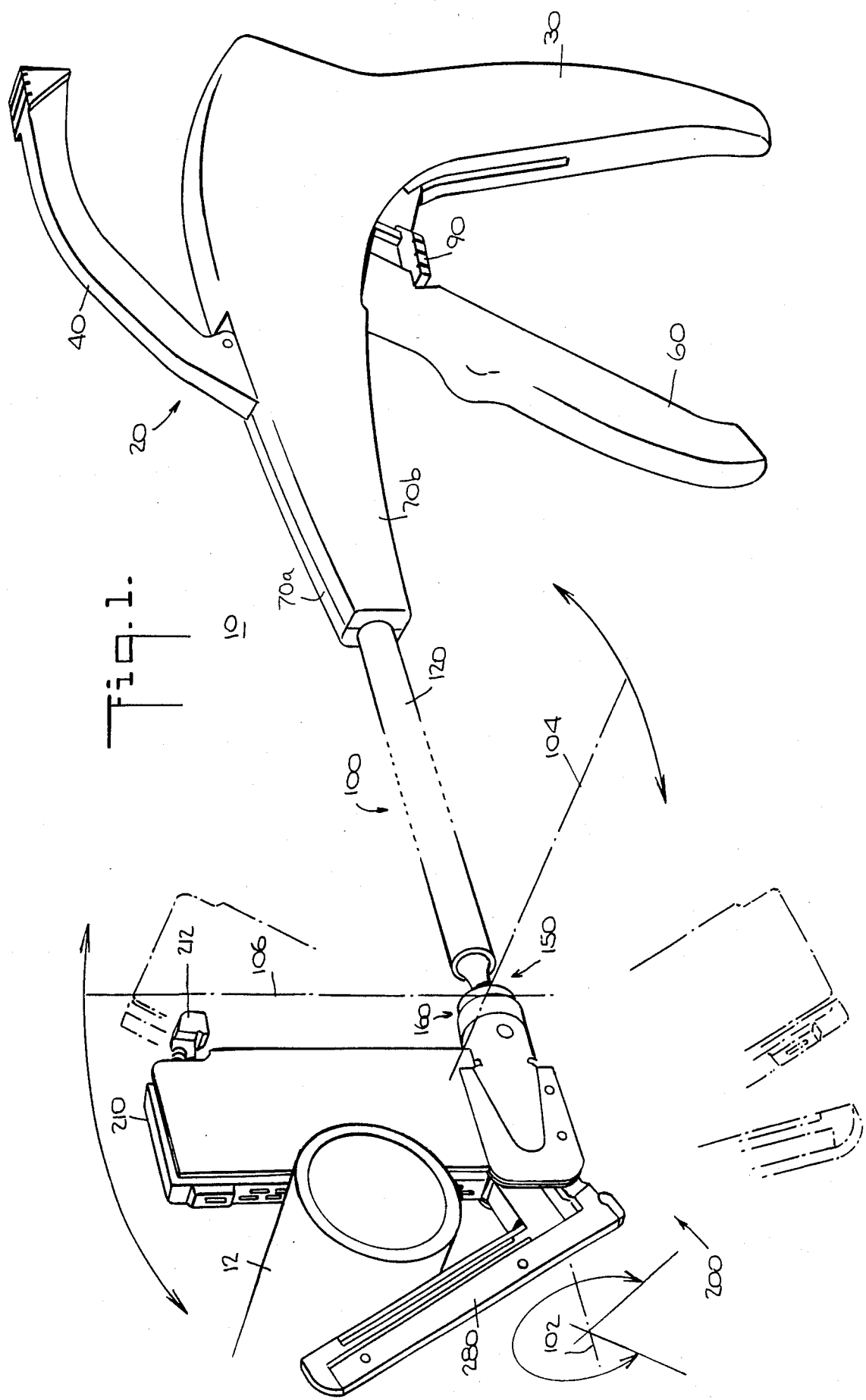
FIG. 1 is a perspective view of surgical fastener applying apparatus which can be modified in accordance with the principles of this invention.

As shown in FIG. 1, a surgical fastener applying instrument 10 which can be modified in accordance with the present invention includes proximal actuator assembly 20, distal fastener applying assembly 200, and intermediate shaft assembly 100.

Fastener applying assembly 200 includes proximal fastener holding part 210 and distal anvil part 280. Anvil part 280 is mounted for limited pivotal and translational motion relative to fastener holding part 210 so that anvil part 280 can be translated and pivoted away from fastener holding part 210 as shown in solid lines in FIG. 1 to permit the tissue 12 that is to be fastened to be inserted between the distal surface of fastener holding part 210 and the proximal surface of anvil part 280.

Fastener holding part 210 is connected to the distal end of shaft assembly 100 just beyond an articulation or joint 150 in the shaft assembly. In the depicted apparatus, joint 150 comprises a spherical ball 152 (FIG. 2) rotatably secured in a complementary socket 160. Joint 150 allows fastener applying assembly 200 to rotate about each of three mutually orthogonal axes 102, 104, and 106, all of which intersect at the center of ball 152. A few of the possible positions of fastener applying assembly 200 are suggested in phantom lines in FIG. 1. The proximal end of shaft assembly 100 may also be rotatably mounted in actuator assembly 20 for additional rotational motion of assemblies 100 and 200 about axis 102, which is the longitudinal axis of the instrument. Other than joint 150 and the rotational mounting of shaft assembly 100 in actuator assembly 20, shaft assembly 100 is substantially rigid transverse to its longitudinal axis. Shaft assembly 100 is also substantially rigid parallel to axis 102.

Actuator assembly 20 includes proximal handle 30, manually operable clamp actuator lever 40, and manually operable fastener actuator lever 60. Pivoting clamp actuator lever 40 down into actuator assembly 20 pulls the lower portion of anvil part 280 toward fastener holding part 210. Squeezing fastener actuator lever 60 toward handle 30 causes fastener holding part 210 to drive the surgical fasteners contained in that part in the distal direction toward anvil part 280. Fastener actuator lever 60 cannot be operated until safety latch 90 is pivoted down away from lever 60 as shown in phantom lines in FIG. 3.

Figure 2:
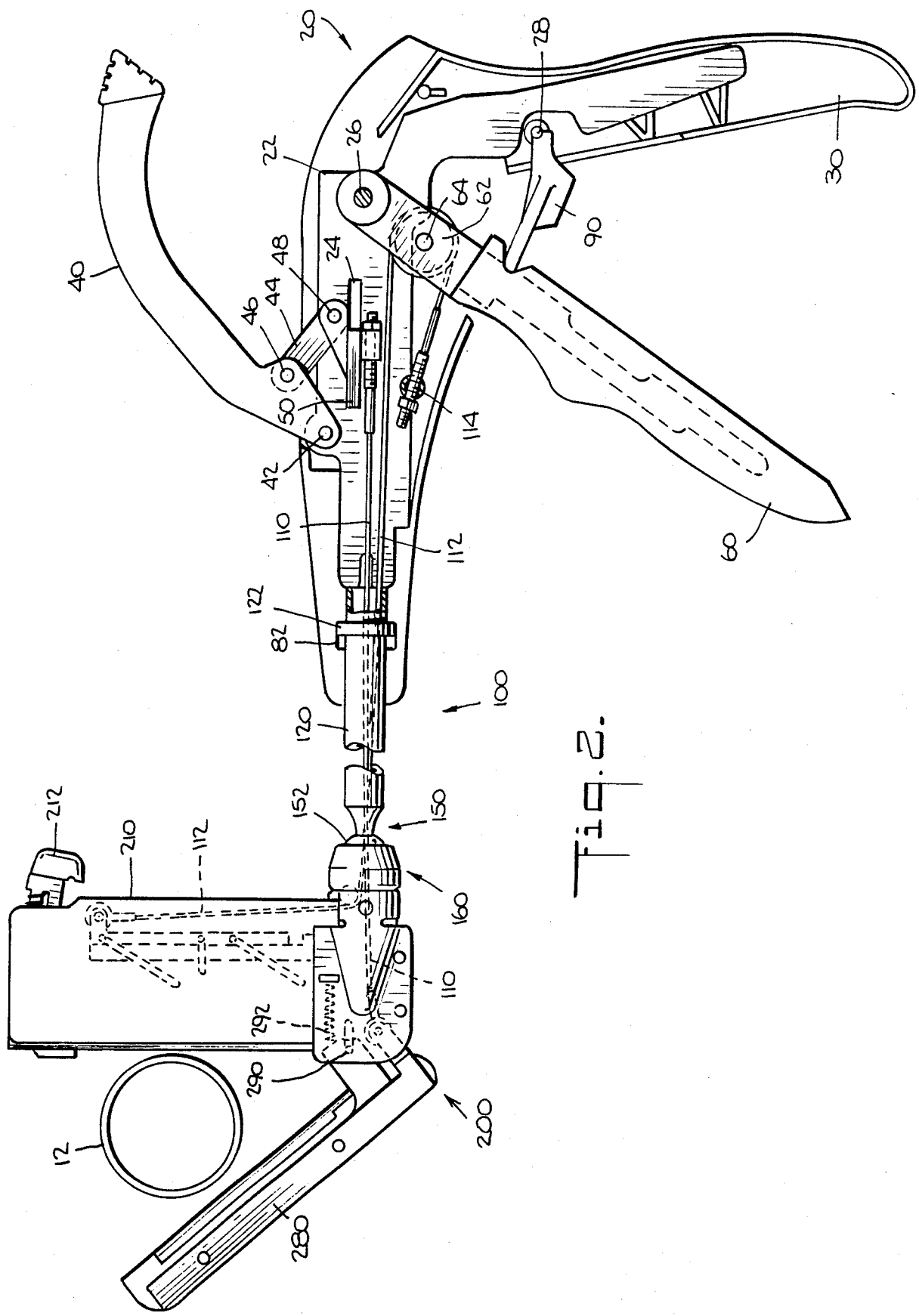
FIG. 2 is a partial, partly sectional, elevational view of the apparatus of FIG. 1 showing an initial stage in the operating cycle of that apparatus.
Figure 8:
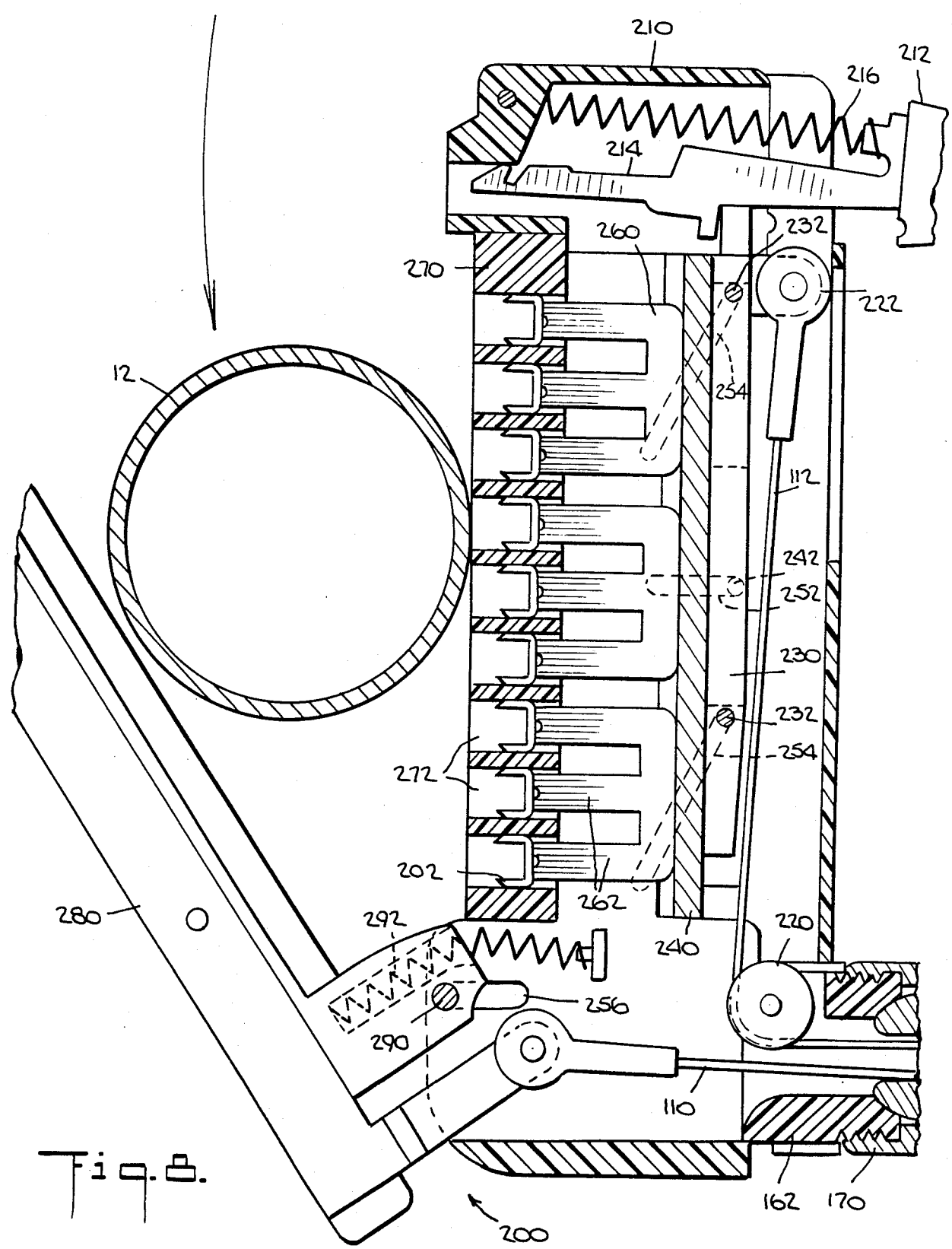
FIG. 8 is a partly sectional, elevational view of a portion of the apparatus of FIGS. 1-7 showing an initial stage in the operating cycle of that apparatus.

Before considering the construction of the apparatus in more detail, a brief description of its overall operation will be given. The initial condition of the apparatus is shown in FIGS. 1, 2, and 8. Fastener applying assembly 200 is rotated, if desired, by any desired amount about any of axes 102, 104, and 106 so that fastener applying assembly 200 has any desired angular orientation relative to actuator assembly 20. Joint 150 and the rotational connection between shaft assembly 100 and actuator assembly 20 are preferably tight enough so that during subsequent operation of the apparatus, assemblies 20 and 200 maintain whatever relative angular orientation they are placed in.

Figure 9:
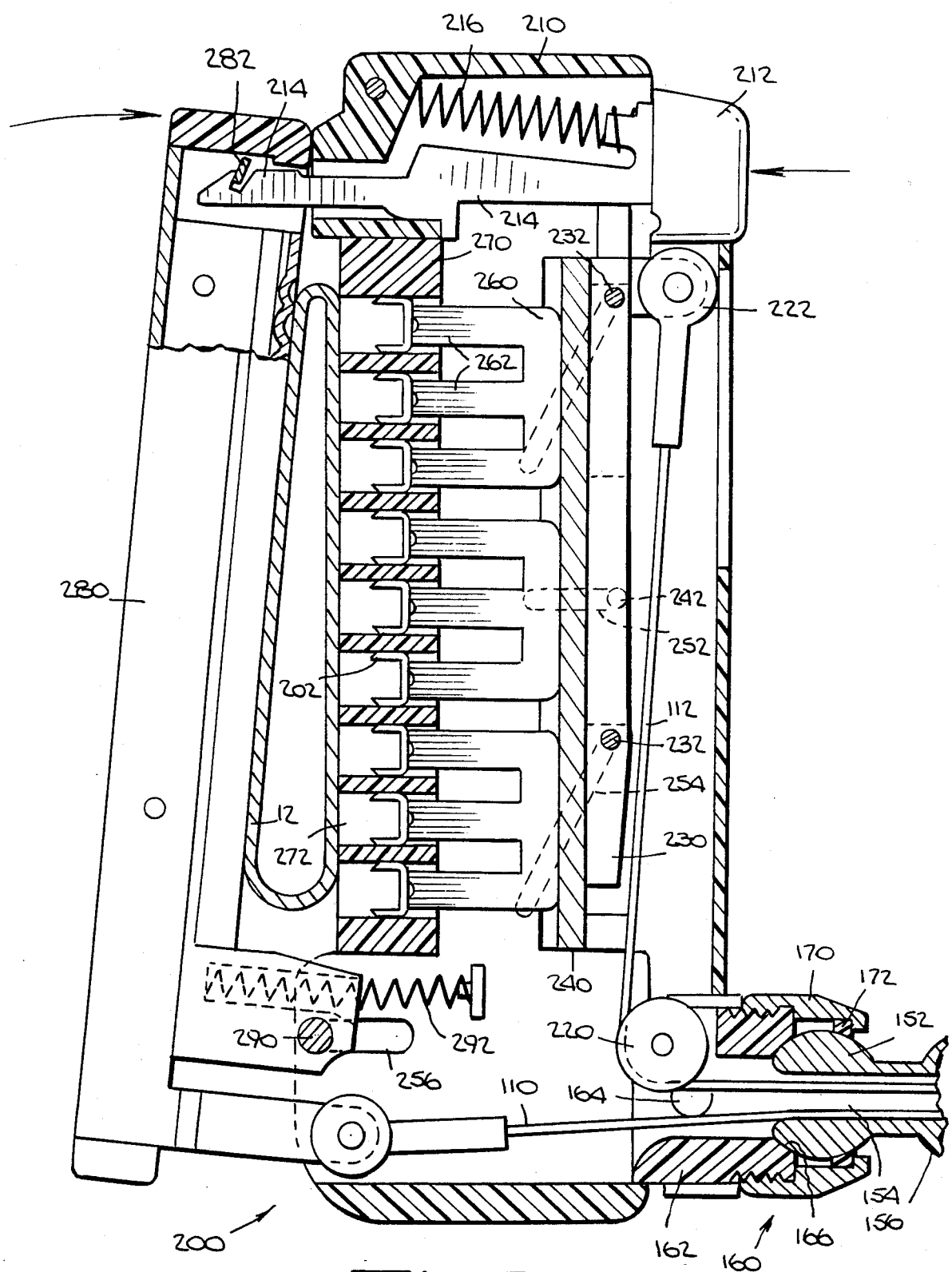
FIGS. 9-12 are views similar to FIG. 8 showing successive stages in the operating cycle of the apparatus.

The tissue 12 to be fastened is placed between anvil part 280 and fastener holding part 210. The upper portion of anvil part 280 is manually moved toward the opposite upper portion of fastener holding part 210 as shown in FIG. 9, and latch button 212 is manually pushed in the distal direction so that latch 214 engages catch 282 in anvil part 280. This holds the upper end of anvil part 280 against the upper end of fastener holding part 210 to begin the clamping of the tissue between those parts.

Figure 3:
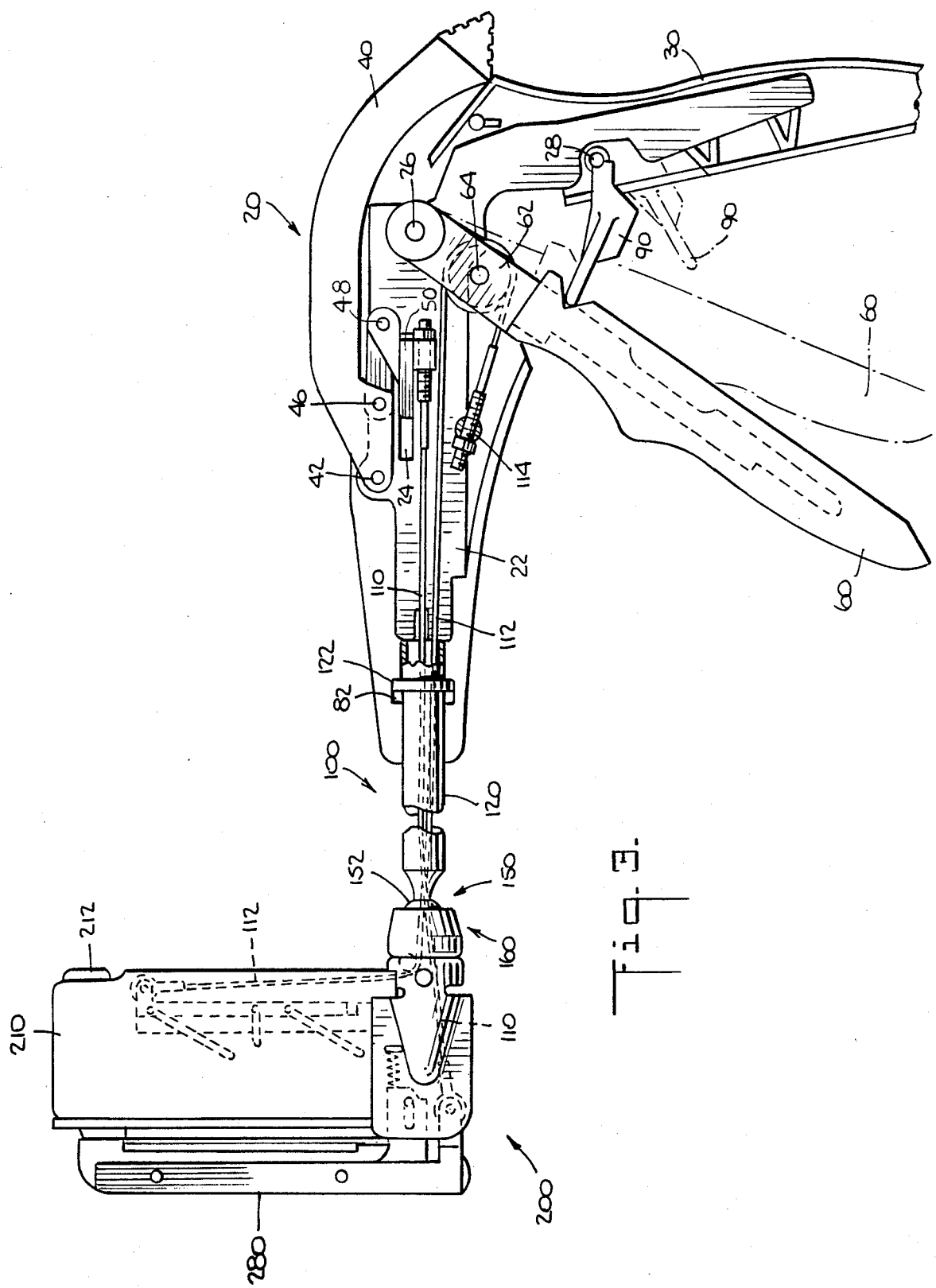
Figure 10:
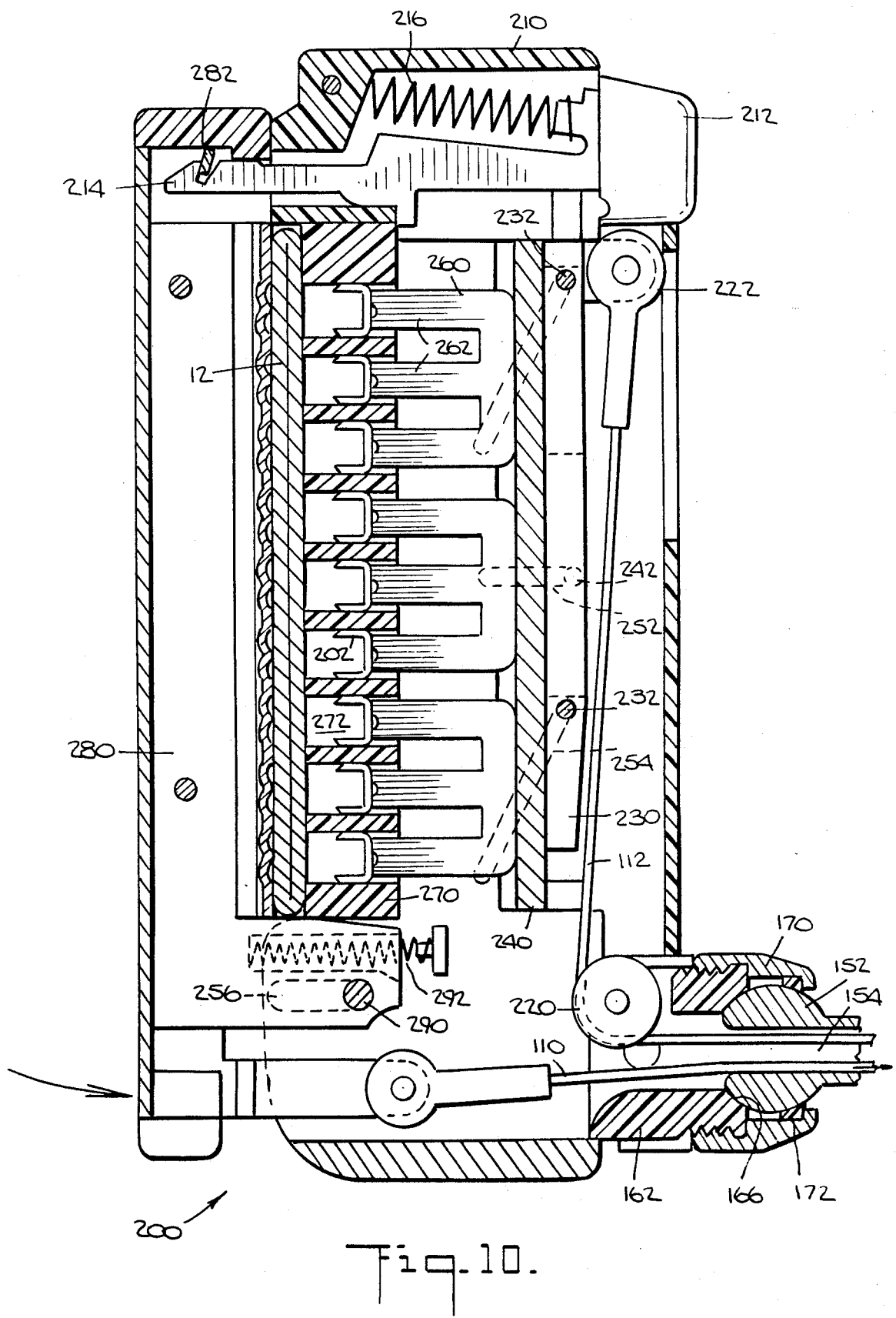

The next operating step is to pivot clamp actuator lever 40 down into actuator assembly 20 as shown in FIG. 3. This pulls the lower end of anvil part 280 in against the lower end of fastener holding assembly 210 as shown in FIGS. 3 and 10. Parts 210 and 280 are now substantially parallel to one another with tissue 12 firmly clamped between the opposing surfaces of those parts. The tissue is now ready to be fastened.

Figure 11:
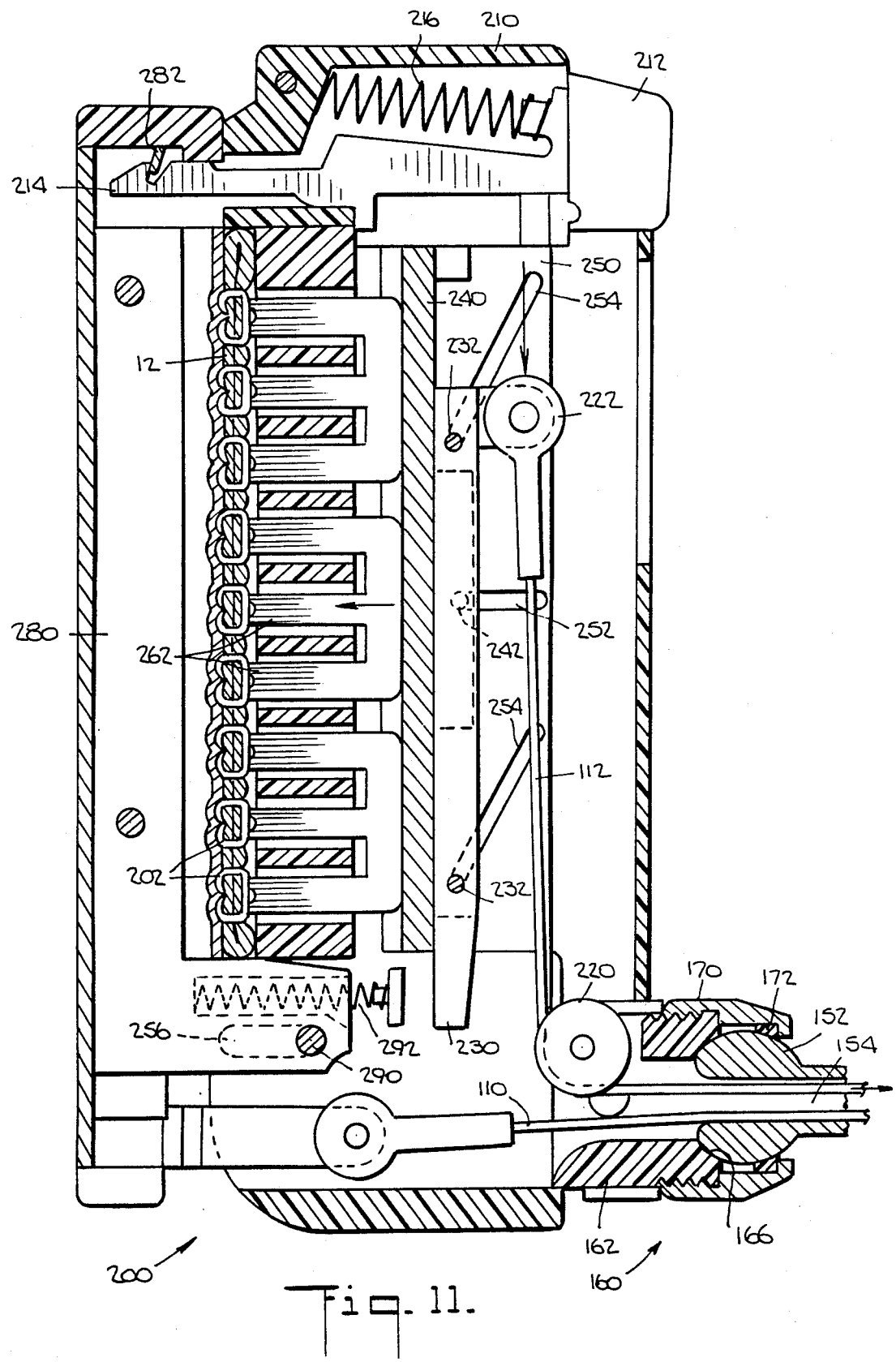

When the fasteners are to be applied, safety latch 90 is pivoted down as indicated in phantom lines in FIG. 3. Fastener actuator lever 60 is then pivoted toward handle 30 as also shown in phantom lines in FIG. 3. This causes fastener holding assembly 210 to simultaneously or substantially simultaneously drive the legs of a plurality of metal surgical staples 202 through tissue 12 and against anvil part 280 as shown in FIG. 11. Anvil part 280 clinches or crimps the ends of the staple legs to secure the staples in the tissue. (Although metal staples are employed in the depicted apparatus, it will be understood that two-part plastic fasteners, such as those shown in Green U.S. Pat. No. 4,402,445, can alternatively be used.) The tissue fastening procedure is now complete.

Figure 12:
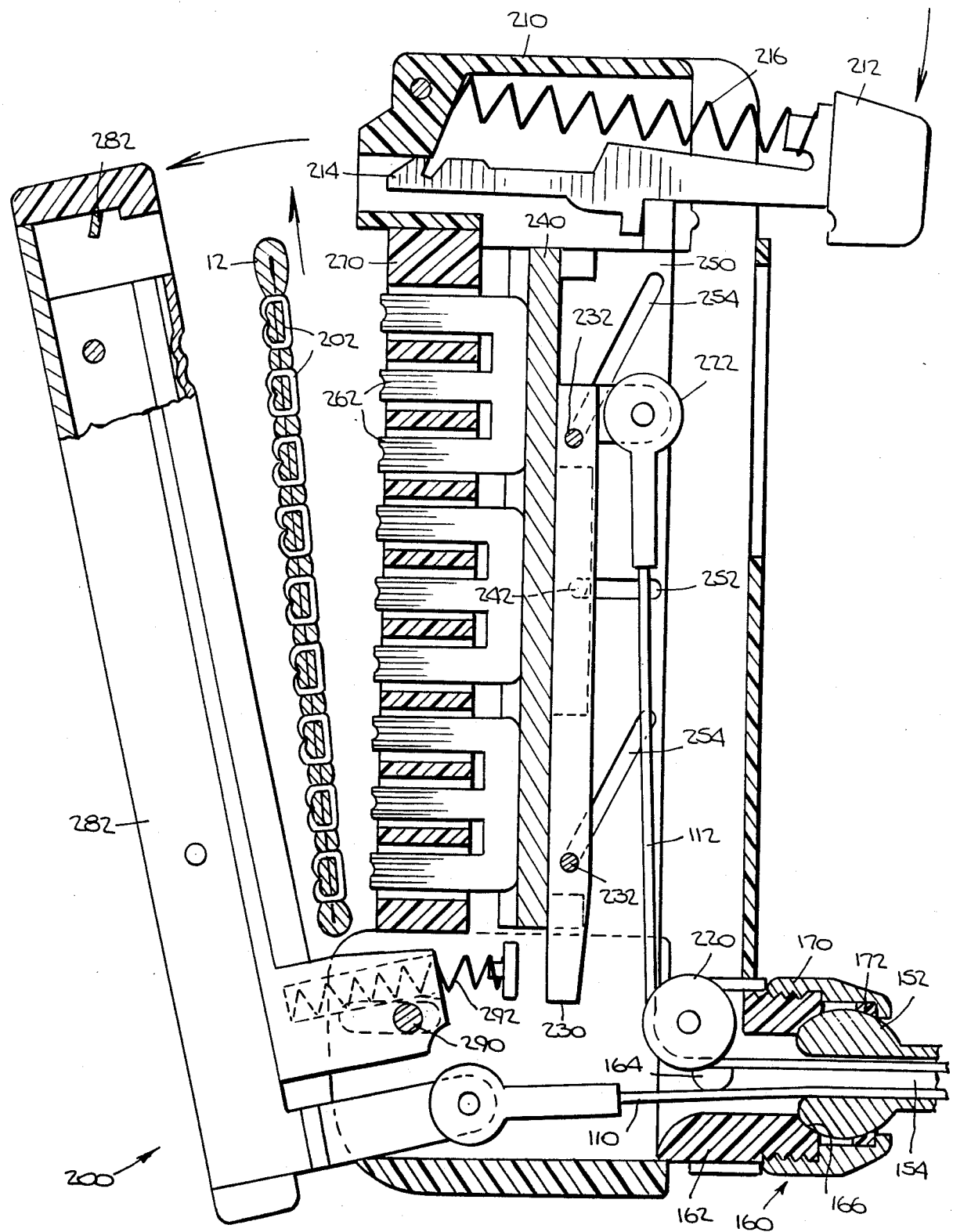

The fastened tissue is removed from the apparatus by manually pushing up on latch button 212 as shown in FIG. 12. This causes latch 214 to release catch 282, thereby allowing anvil part 280 to pivot away from fastener holding part 210. The fastened tissue can now be removed from the apparatus.

Figure 4:
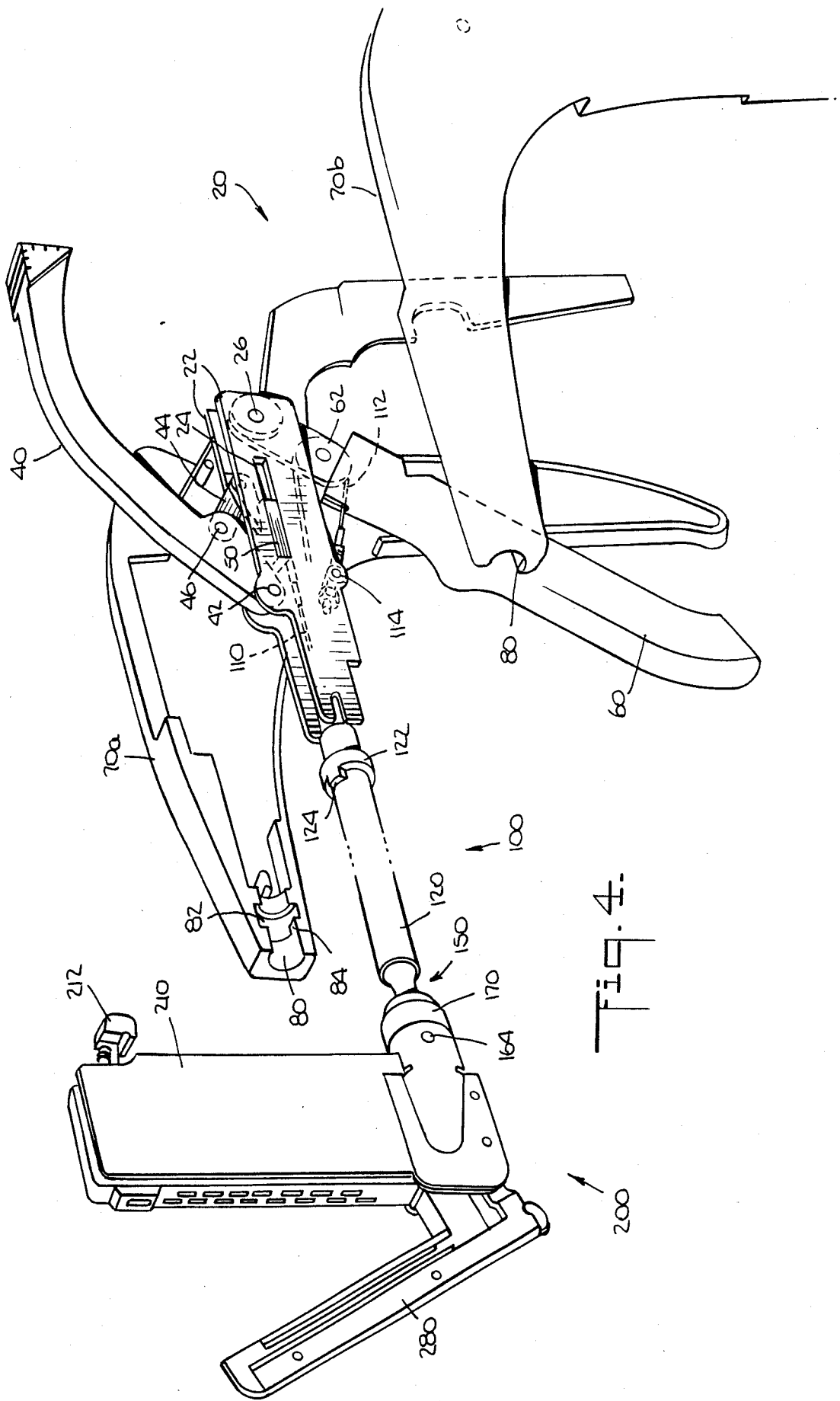
FIG. 4 is a view similar to FIG. 2 but showing a subsequent stage in the operating cycle.

Considering now the internal construction and operation of the apparatus, first with reference to FIG. 2, clamp actuator lever 40 is pivotally connected to actuator assembly frame 22 by pivot pin 42. One end of toggle link 44 is pivotally connected to lever 40 by pin 46. The other end of toggle link 44 is pivotally connected to slide 50 by pin 48. Slide 50 is mounted for longitudinal reciprocal motion in slots 24 in frame 22 (see also FIG. 4). When lever 40 is pivoted out from the remainder of actuator assembly 20 as shown in FIGS. 2 and 4, slide 50 is in its distal position in slots 24. When lever 40 is pivoted down toward the remainder of actuator assembly 20 as shown in FIG. 3, slide 50 moves proximally in slots 24. In the fully operated position of lever 40, pin 46 has moved slightly past a straight line through pins 42 and 48 so that lever 40 tends to remain in the fully operated position.

The proximal end of a first transversely flexible member 110 is connected to slide 50. Member 110 may be a metal wire or cable, and for convenience herein, member 110 will be referred to as cable 110. Cable 110 passes through the hollow tubular shaft 120 which is the outer member of most of the length of shaft assembly 100. Cable 110 also passes through longitudinal aperture 154 (FIG. 7) in ball 152 and into fastener applying assembly 200. The distal end of cable 110 is connected to anvil part 280 (see also FIG. 5). Accordingly, when lever 40 is pivoted down toward the remainder of actuator assembly 20, cable 110 pulls the lower end of anvil part 280 in toward fastener holding part 210. Cable 110 is transversely flexible so that it does not interfere with the pivoting of joint 150. It should also be noted that cable 110 passes through the point of intersection of axes 102, 104, and 106 (FIG. 1) so that even when placed in tension by operation of lever 40, cable 110 does not tend to alter the relative rotational orientation of assemblies 20 and 200.

Figure 5:
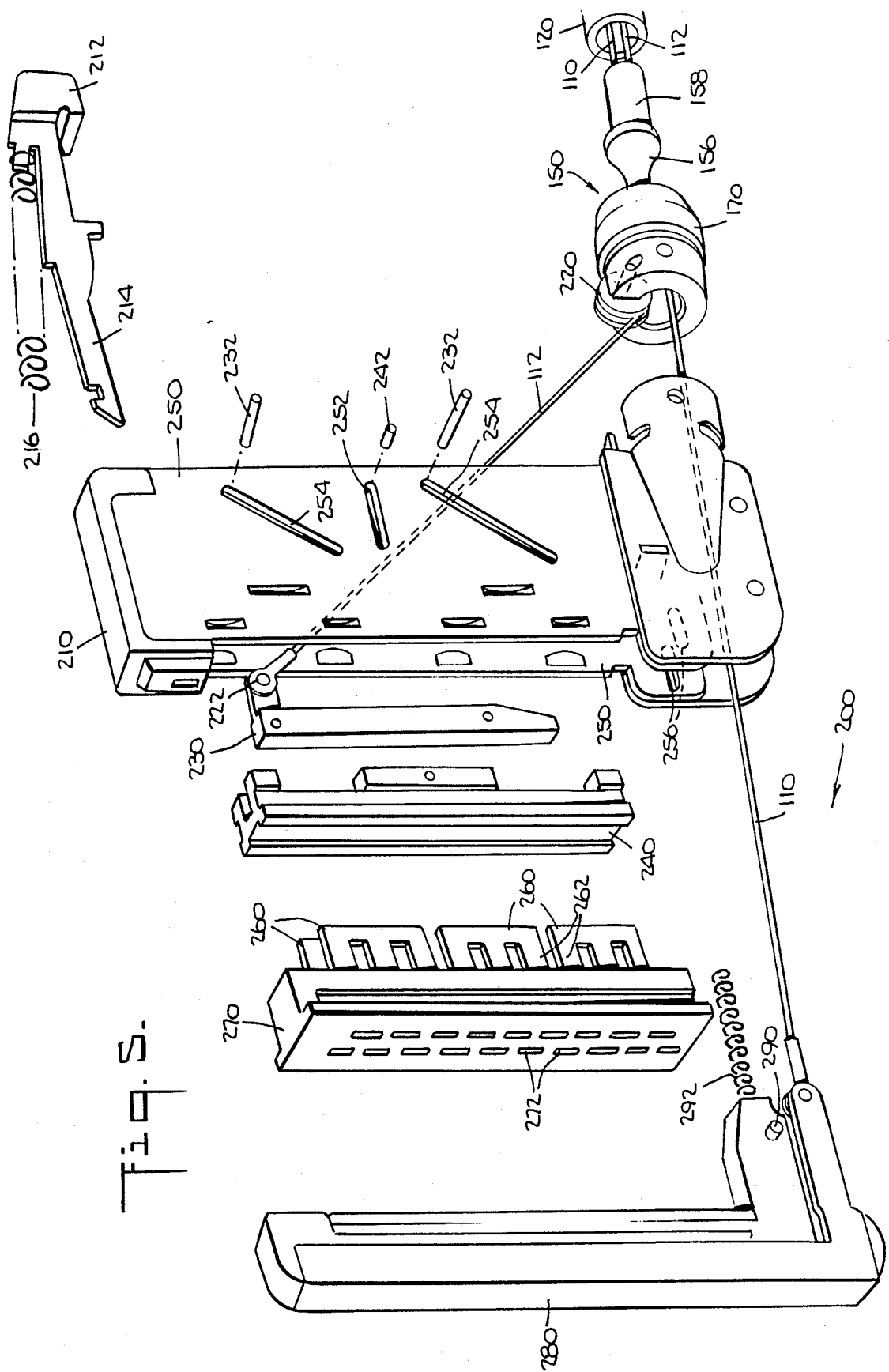
FIGS. 5-7 are exploded perspective views of various portions of the apparatus of FIGS. 1-4.

Returning to FIG. 2, fastener actuator lever 60 is pivotally connected to frame 22 by pin 26. Safety latch 90 is similarly pivotally connected to handle 30 by pin 28. The proximal end of a second transversely flexible member 112 is fixedly attached to frame 22 at anchor 114. Member 112 may be similar to cable 110 and is therefore referred to as cable 112. A proximal portion of cable 112 passes around roller 62 which is rotatably mounted on lever 60 by means of axle 64. After passing roller 62, cable 112 passes distally through shaft 120 and joint 150 and into fastener holding part 210. As is best seen in FIGS. 5 and 8, as cable 112 enters fastener holding part 210, it passes around roller 220. Roller 220 redirects cable 112 up to anchor 222 which connects the distal end of cable 112 to cam bar 230. Accordingly, when lever 60 is pivoted toward handle 30, cable 112 pulls down on cam bar 230. Like cable 110, cable 112 passes through the point of intersection of axes 102, 104, and 106 and is sufficiently transversely flexible so that it does not interfere with the pivoting of joint 150 or tend to alter the relative rotational orientation of assemblies 20 and 200 even when placed in tension by operation of lever 60.

Figure 6:
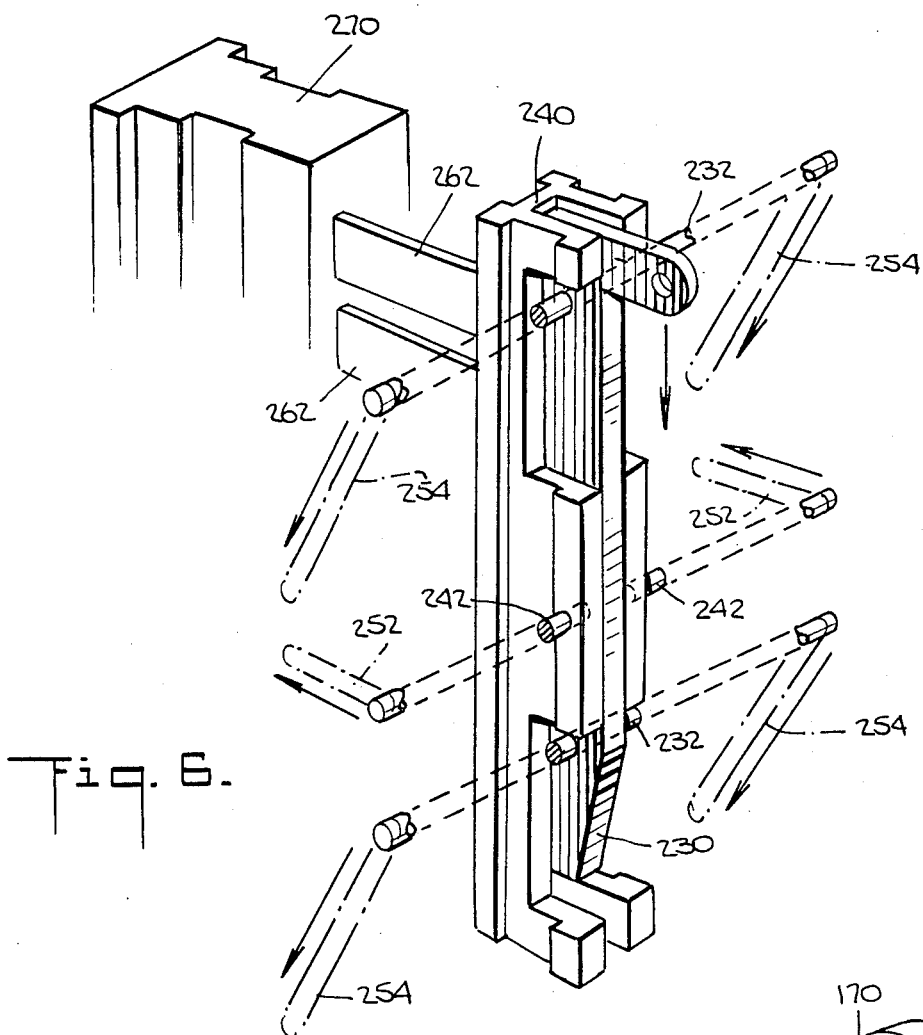

Cam bar 230 is disposed in a proximal-facing channel in pusher actuator member 240 (see FIG. 6). The distal face of cam bar 230 bears on and is slidable along the bottom of this channel in member 240. Pusher actuator member 240 is disposed between two parallel, laterally spaced frame members 250 (FIG. 5) of fastener holding part 210. The distal surface of pusher actuator member 240 bears on the proximal ends of pusher members 260 which have pusher fingers 262 extending into apertures 272 in fastener holder 270 behind staples 202. Pusher actuator member 240 is constrained to move substantially parallel to the axis along which staples 202 are driven by pusher members 260. This constraint is provided by guide pins 242 which extend laterally outward from member 240 into guide slots 252 in frame members 250. It should be noted that pusher actuator member 240 can also pivot about pins 242.

As cam bar 230 is pulled down by cable 112, it is also forced to move in the distal direction by operation of cam follower pins 232 which pass through cam bar 230 and project laterally into cam slots 254 in frame members 250. Cam slots 254 are inclined so that as cam bar 230 moves down in response to the motion of cable 112, it also moves distally. Cam bar 230 slides longitudinally along pusher actuator member 240 so that only the distal motion of cam bar 230 is imparted to member 240. As member 240 moves distally, it drives pusher members 260 and therefore staples 202 in the distal direction. Thus elements 230, 232, 240, 242, 250, 252, 254, and 260 constitute means for converting the downward motion of the distal end of cable 112 into distal motion of staples 202.

The connection between shaft assembly 100 and actuator assembly 20 which permits relative rotation of those assemblies is best seen in FIG. 4. The proximal end of shaft 120 is rotatably mounted in a cylindrical socket 80 formed in the two mirror image halves 70a and 70b of the outer shell of actuator assembly 20. Shell halves 70 are held together by any suitable means such as rivets, adhesive, or the like. Annular collar 122 on shaft 120 is received in annular enlargement 82 of socket 80 to retain shaft 120 in the proper longitudinal position relative to actuator assembly 20. If desired, the amount of rotation of shaft 120 relative to actuator assembly 20 may be limited by cooperating stops 124 on shaft 120 and 84 on actuator assembly shell 70. Shell halves 70 preferably engage shaft 120 with sufficient force to frictionally maintain the relative angular orientation of shaft 120 and actuator assembly 20 established by the user of the apparatus.

Figure 7:
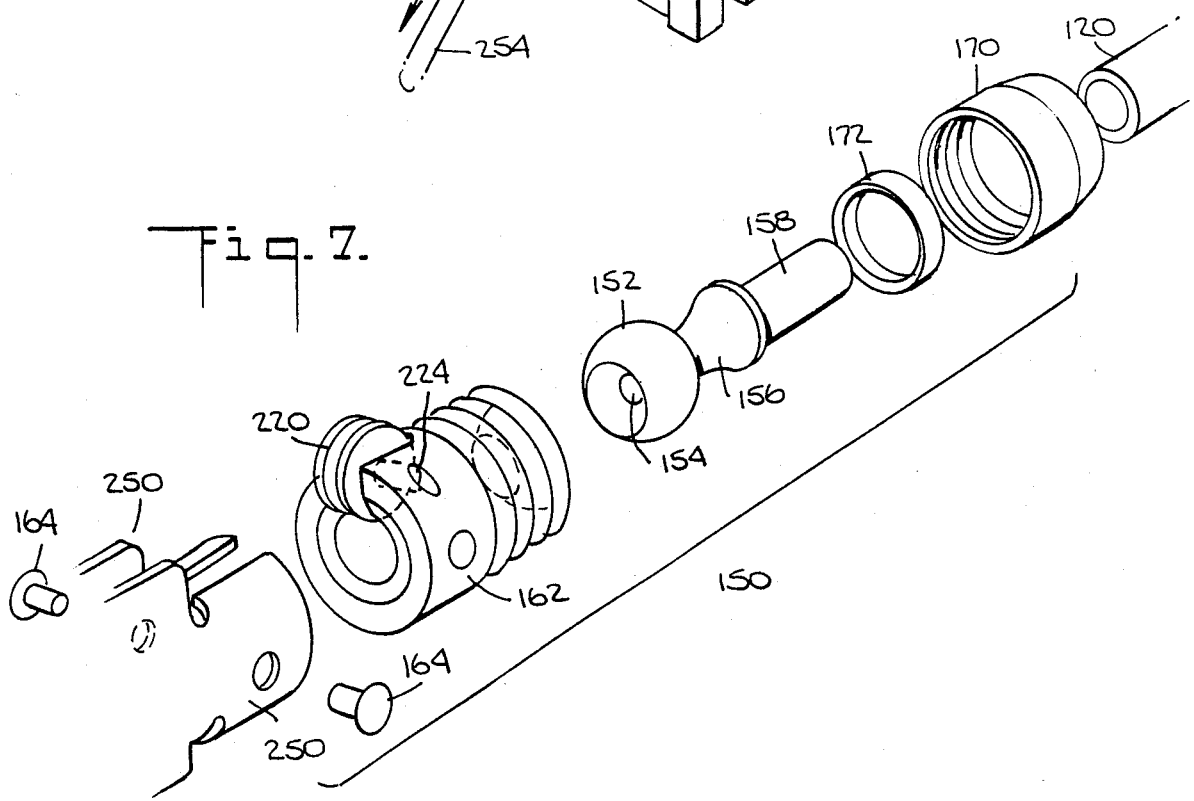

The detailed construction of joint 150 is shown in FIG. 7. Ball 152 is formed at the distal end of hollow, generally frustoconical pedestal 156. A hollow cylindrical shank 158 extends proximally from the base of pedestal 156. Shank 158 is force-fitted into the distal end of shaft 120. Ball 152 fits snugly into socket 160, the construction of which is best seen in FIG. 9. Socket 160 includes distal seat member 162 which carries roller 220 on axle 224 and which is fixedly attached to frame members 250 by pins 164 (FIG. 7). Seat member 162 is hollow and has a proximal-facing annular seat surface 166 for receiving the distal end portion of ball 152. The proximal portion of the cylindrical outer surface of seat member 162 is threaded to receive collar 170. Collar 170 forces an annular retaining ring 172 against a proximal portion of the surface of ball 152. Accordingly, ball 152 is captured between seat surface 166 and retaining ring 172 but can rotate relative to those members about each of axes 102, 104, and 106. Surfaces 166 and 172 preferably engage ball 152 with sufficient force to frictionally maintain whatever relative angular orientation of assemblies 20 and 200 is established by the user of the apparatus. In a particularly preferred embodiment, ball 152 is steel and members 162 and 172 are made of a thermoplastic material such as nylon.

Anvil part 280 is pivotally connected to fastener holding part 210 by means of pin 290 in elongated slots 256 in frame members 250. Slots 256 are elongated parallel to the longitudinal axis of the apparatus so that anvil part 280 can both pivot about pin 290 and translate parallel to slots 256. Anvil part 280 is resiliently biased away from fastener holding part 210 by compression coil spring 292 which is compressed between those parts. Latch 214 is resiliently biased in the proximal direction as shown, for example, in FIG. 8 by compression coil spring 216 acting between latch 214 and the body of fastener holding part 210.

Figure 13:
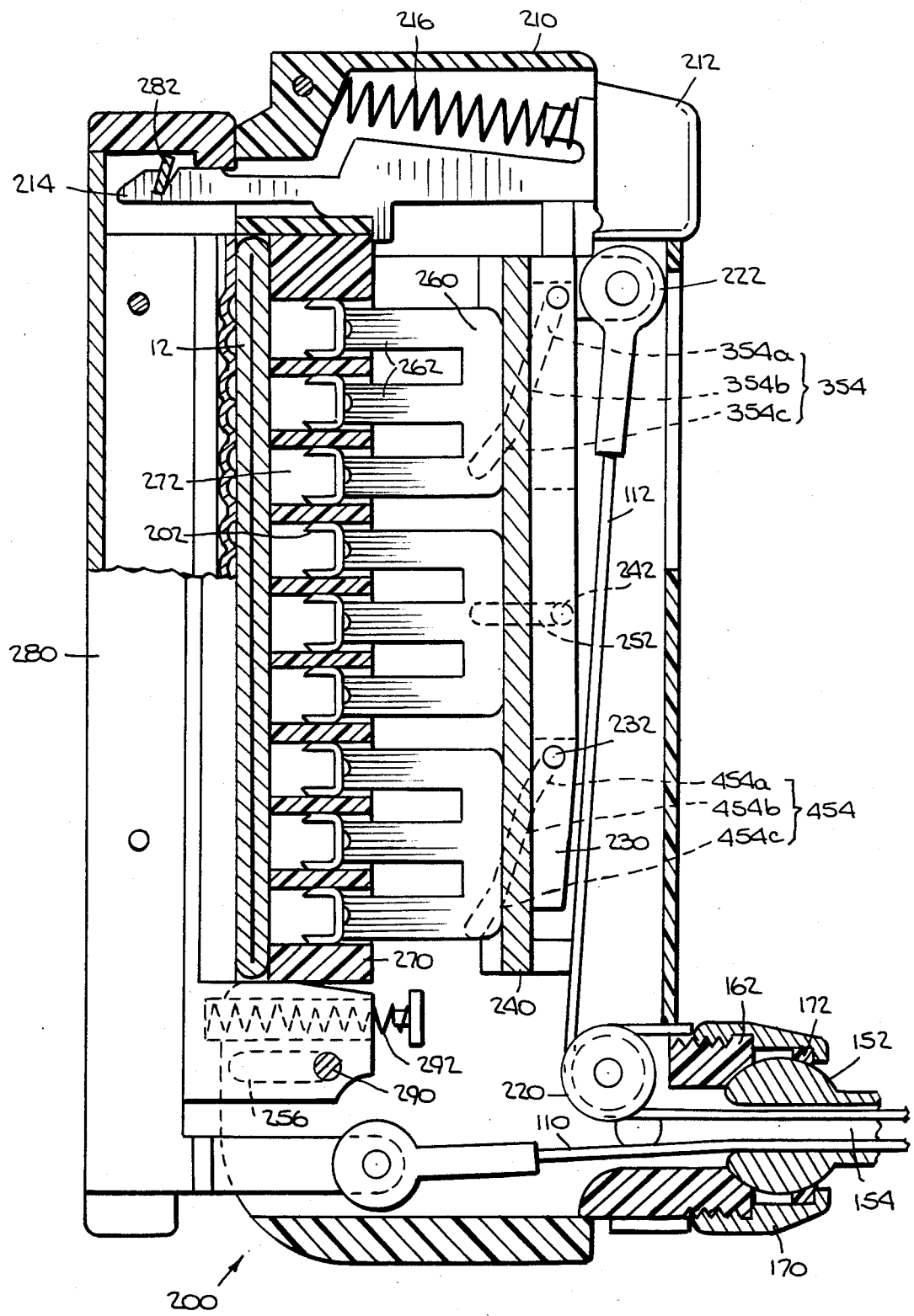
FIG. 13 is a view similar to FIG. 10 showing how the apparatus of FIGS. 1-12 can be modified in accordance with the present invention.

The above-described apparatus can be modified in accordance with the present invention as shown in FIG. 13. Instead of the four identical cam slots 254 employed in the apparatus of FIGS. 1-12, in FIG. 13 the two upper cam slots 354 (only one of which is visible in FIG. 13) may be identical to one another but different from the two identical lower cam slots 454 (only one of which is visible in FIG. 13). In particular, each of lower cam slots 454 has an initial portion 454a which is more steeply inclined in the distal direction than the corresponding initial portion 354a of upper cam slots 354. This causes the lower end of cam bar 230 and the lower end of pusher actuator member 240 to initially move more rapidly in the distal direction than the upper ends of those members. This in turn causes the staples 202 near the bottom of fastener holding part 210 to advance more rapidly toward tissue 12 than the staples 202 near the top of fastener holding part 210. Accordingly, the ends of the staple legs do not all reach anvil part 280 at the same time. Rather, the staples near the bottom of fastener holding part 210 reach anvil part 280 first and begin to clinch against the anvil part before the staples near the top. The maximum force or "peak load" for clinching each staple therefore tends to occur at a different time than the peak loads for clinching the other staples. This distributes over time the individual staple-clinching peak loads, thereby reducing the aggregate total peak load required to drive the staples.

Following their initial portions 354a and 454a, each of cam slots 454 has an intermediate portin 454b which is substantially parallel to or slightly less steeply inclined in the distal direction than the corresponding intermediate portions 354b of cam slots 354. This maintains the condition of the apparatus in which the lower portions of elements 230 and 240 are more distally advanced than the upper portions of those elements until most or all of staples 202 have at least begun to clinch and have therefore passed their peak load requirement.

The final segments 354c and 454c of cam slots 354 and 454 may be somewhat more steeply inclined in the distal direction than the intermediate segments. These final segments are traversed by cam follower pins 232 during the final compression of staples 202 when the force required is substantially less than the peak load. The angle of inclination of cam slot segments 354c may differ from the angle of inclination of cam slot segments 454c so that when both cam follower pins 232 have reached the end of their travel, they will both have moved the same distal distance from their starting positions. This assures that, although during the staple driving stroke members 230 and 240 are deliberately inclined relative to the (vertical) longitudinal axis of anvil part 280, the staple driving stroke ends with members 230 and 240 substantially parallel to that axis. This provides uniform compression of all of the staples.

Although the invention has been illustrated in the context of surgical fastener applying instruments which apply two parallel rows of surgical fasteners, the greater the number of fasteners to be applied, the greater the advantages of the invention become. For example, the invention is even more beneficial in instruments which apply four parallel rows of surgical fasteners as shown, for example, in Green U.S. Pat. No. 4,402,444.

It is to be understood that the invention is not limited in application to surgical fastener applying apparatus of the type shown in FIGS. 1-12 herein. For example, although that apparatus has an articulated shaft assembly, the present invention is equally applicable to instruments with other types of shaft assemblies such as transversely flexible or completely rigid shaft assemblies. Similarly, although metal surgical staples 202 are employed in the depicted apparatus, other types of surgical fasteners, such as two-part plastic fasteners like those shown in Green U.S. Pat. No. 4,402,445, could be used instead. Also, either the metal staples or the plastic fasteners employed can be either biologically inert or biologically absorbable, as is now well known to those skilled in the art.

I claim:

1. Apparatus for applying a longitudinal array of surgical fasteners to body tissue comprising:
   a plurality of surgical fasteners in a longitudinal array;
   fastener pusher means for pushing the fasteners into the tissue along an axis transverse to the longitudinal array, the fastener pusher means including a first rigid longitudinal member parallel to and coextensive with the longitudinal array;
   a second member for supplying the work required for pushing the fasteners into the tissue; and
   first means for transmitting the work supplied by the second member to the first member so that one end of the first member initially moves parallel to the transverse axis substantially faster than the other end of the first member to cause the fasteners adjacent said one end of the first member to be applied to the tissue in advance of the fasteners adjacent said other end of the first member.

2. The apparatus defined in claim 1 wherein the first means includes second means for increasing the rate of motion of said other end of the first member parallel to the transverse axis as the fasteners are applied.

3. The apparatus defined in claim 2 wherein the first and second means cooperate so that both ends of the first member have moved substantially the same distance parallel to the transverse axis when all the work supplied by the second member has been transmitted to the first member.

4. The apparatus defined in claim 1 wherein the second member supplies the work required for pushing the fasteners into the tissue by moving with a component of motion substantially parallel to the longitudinal array.

5. The apparatus defined in claim 4 further comprising:
   a third member; and
   third means for mounting the first member relative to the third member so that the first member can only move relative to the third member substantially parallel to the transverse axis, the second member being in sliding contact with the first member substantially parallel to the longitudinal array;
   the first means further including first and second cam and cam follower assemblies connected between the second and third members and respectively located adjacent said one and said other end of the first member for causing the second member to move relative to the third member with a component of motion substantially parallel to the transverse axis as the second member moves relative to the third member substantially parallel to the longitudinal array.

6. The apparatus defined in claim 5 wherein the initial portion of the cam surface traversed by the cam follower of the first cam and cam follower assembly is more nearly parallel to the transverse axis than the corresponding cam surface portion of the second cam and cam follower assembly.

7. The apparatus defined in claim 6 wherein after the initial cam surface portion of the first cam and cam follower assembly, there is a portion of said cam surface which is more nearly parallel to the longitudinal array than the corresponding cam surface portion of the second cam and cam follower assembly.

* * * * *